(12) United States Patent
Choa et al.

(10) Patent No.: US 11,573,196 B2
(45) Date of Patent: Feb. 7, 2023

(54) GAS SENSOR COMPRISING COMPOSITE STRUCTURE INCLUDING GRAPHENE AND METAL PARTICLE BONDED TO EACH OTHER AND METHOD FOR MANUFACTURING SAME

(71) Applicant: INDUSTRY-UNIVERSITY COOPERATION FOUNDATION HANYANG UNIVERSITY ERICA CAMPUS, Ansan-Si (KR)

(72) Inventors: Yong Ho Choa, Ansan-si (KR); Tae-Yeon Hwang, Ansan-si (KR); Yo Seb Song, Ansan-si (KR); Se Il Kim, Ansan-si (KR); Gwang Myeong Go, Ansan-si (KR)

(73) Assignee: INDUSTRY-UNIVERSITY COOPERATION FOUNDATION HANYANG UNIVERSITY ERICA CAMPUS, Ansan-si (KR)

(*) Notice: Subject to any disclaimer, the term of this patent is extended or adjusted under 35 U.S.C. 154(b) by 406 days.

(21) Appl. No.: 16/764,068

(22) PCT Filed: Apr. 19, 2018

(86) PCT No.: PCT/KR2018/004527
§ 371 (c)(1),
(2) Date: May 14, 2020

(87) PCT Pub. No.: WO2019/098469
PCT Pub. Date: May 23, 2019

(65) Prior Publication Data
US 2020/0386698 A1 Dec. 10, 2020

(30) Foreign Application Priority Data
Nov. 15, 2017 (KR) .......................... 10-2017-0151984

(51) Int. Cl.
*G01N 27/407* (2006.01)
*G01N 25/22* (2006.01)
(Continued)

(52) U.S. Cl.
CPC ......... *G01N 27/4075* (2013.01); *G01N 25/22* (2013.01); *G01N 25/32* (2013.01);
(Continued)

(58) Field of Classification Search
CPC ........ G01N 25/20; G01N 25/22; G01N 25/32; G01N 27/12; G01N 27/127; G01N 27/4075; G01N 33/005
See application file for complete search history.

(56) References Cited

U.S. PATENT DOCUMENTS

| 2007/0212263 A1 | 9/2007 | Shin et al. |
| 2014/0060607 A1 | 3/2014 | Wu et al. |
| 2016/0013389 A1 | 1/2016 | Choa et al. |

FOREIGN PATENT DOCUMENTS

| JP | 2009-294138 | 12/2009 | |
| JP | 2009294138 A | * 12/2009 | ............. G01N 25/22 |

(Continued)

OTHER PUBLICATIONS

Chu et al., "Hydrogen detection using platinum coated graphene grown on SiC", Sensors and Actuators B 157 pp. 500-503 (2011).

*Primary Examiner* — Benjamin R Schmitt
(74) *Attorney, Agent, or Firm* — Finch & Maloney PLLC

(57) ABSTRACT

Disclosed is a gas sensor. The gas sensor comprises: a substrate; a thermoelectric layer which is disposed on the substrate and has a metal nanowire; a first electrode and a second electrode disposed to be spaced apart from each other on the thermoelectric layer; and a catalyst layer which
(Continued)

is disposed on the first electrode and has a composite structure in which a metal particle is bonded to a carbon structure.

12 Claims, 19 Drawing Sheets

(51) Int. Cl.
  *G01N 33/00* (2006.01)
  *G01N 27/12* (2006.01)
  *G01N 25/32* (2006.01)

(52) U.S. Cl.
  CPC .......... *G01N 27/12* (2013.01); *G01N 27/127* (2013.01); *G01N 33/005* (2013.01)

(56) References Cited

FOREIGN PATENT DOCUMENTS

| KR | 10-2011-0123022 | 11/2011 |
| KR | 10-2013-0094560 | 8/2013 |
| KR | 10-2014-0106812 | 9/2014 |
| KR | 10-1719928 | 3/2017 |
| KR | 10-2017-0112978 | 10/2017 |

* cited by examiner

[FIG. 1]
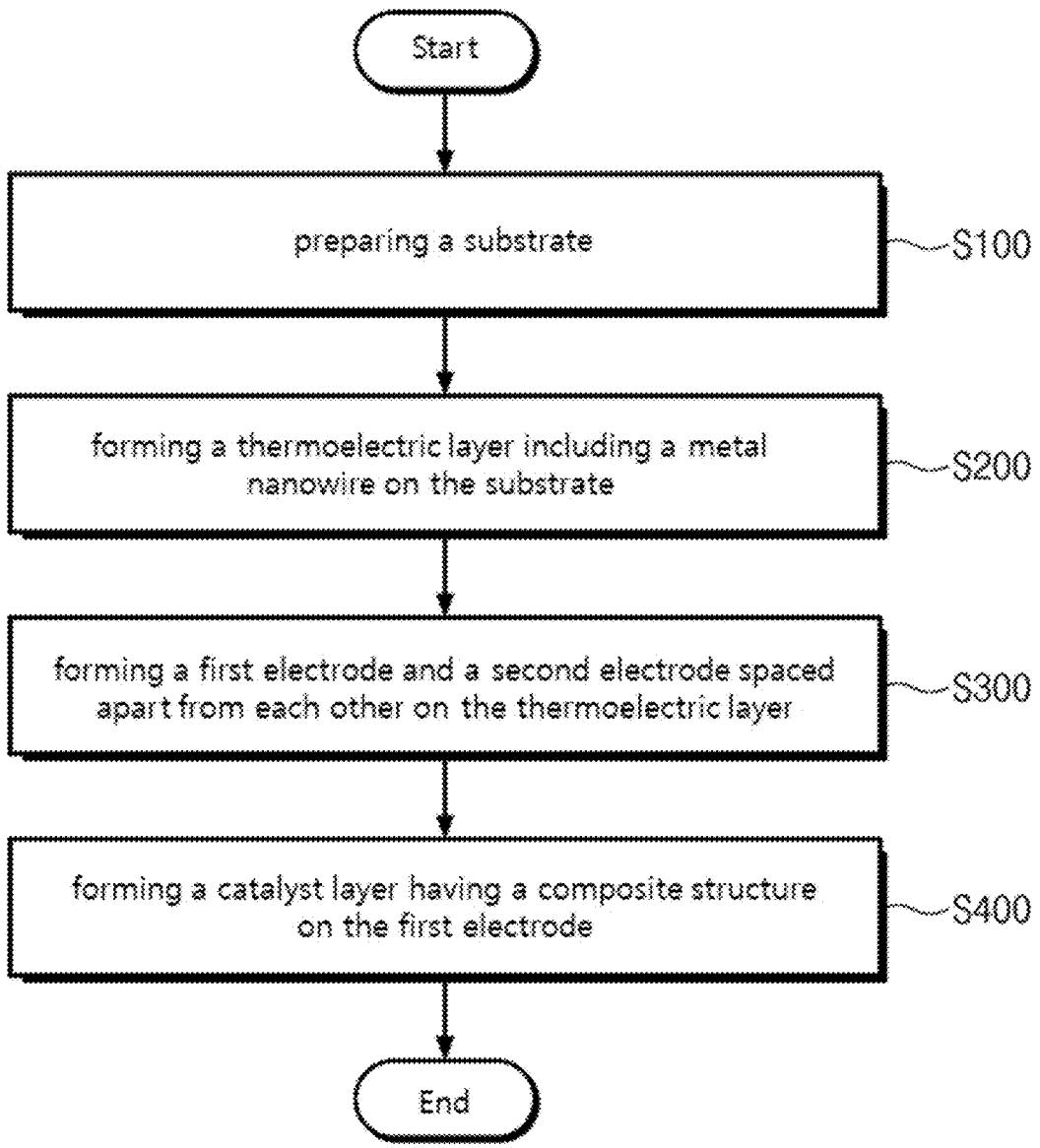

[FIG. 2]
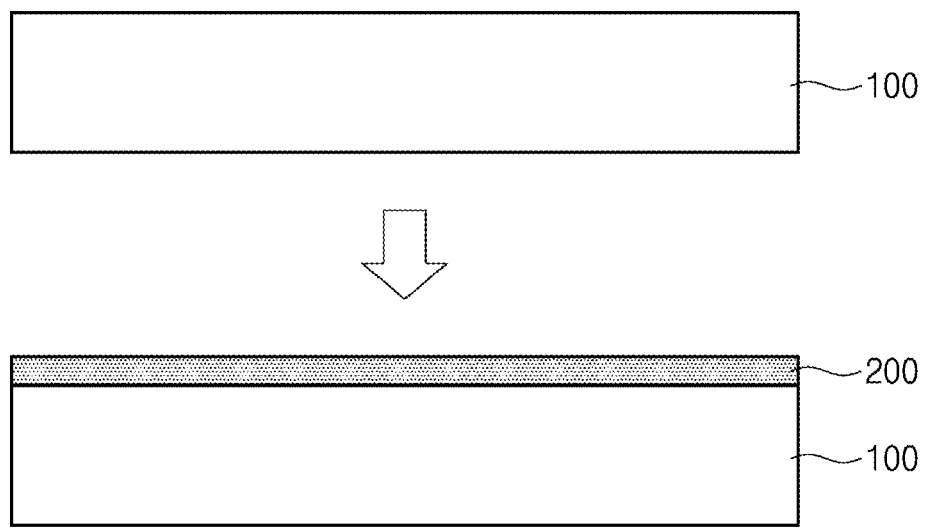

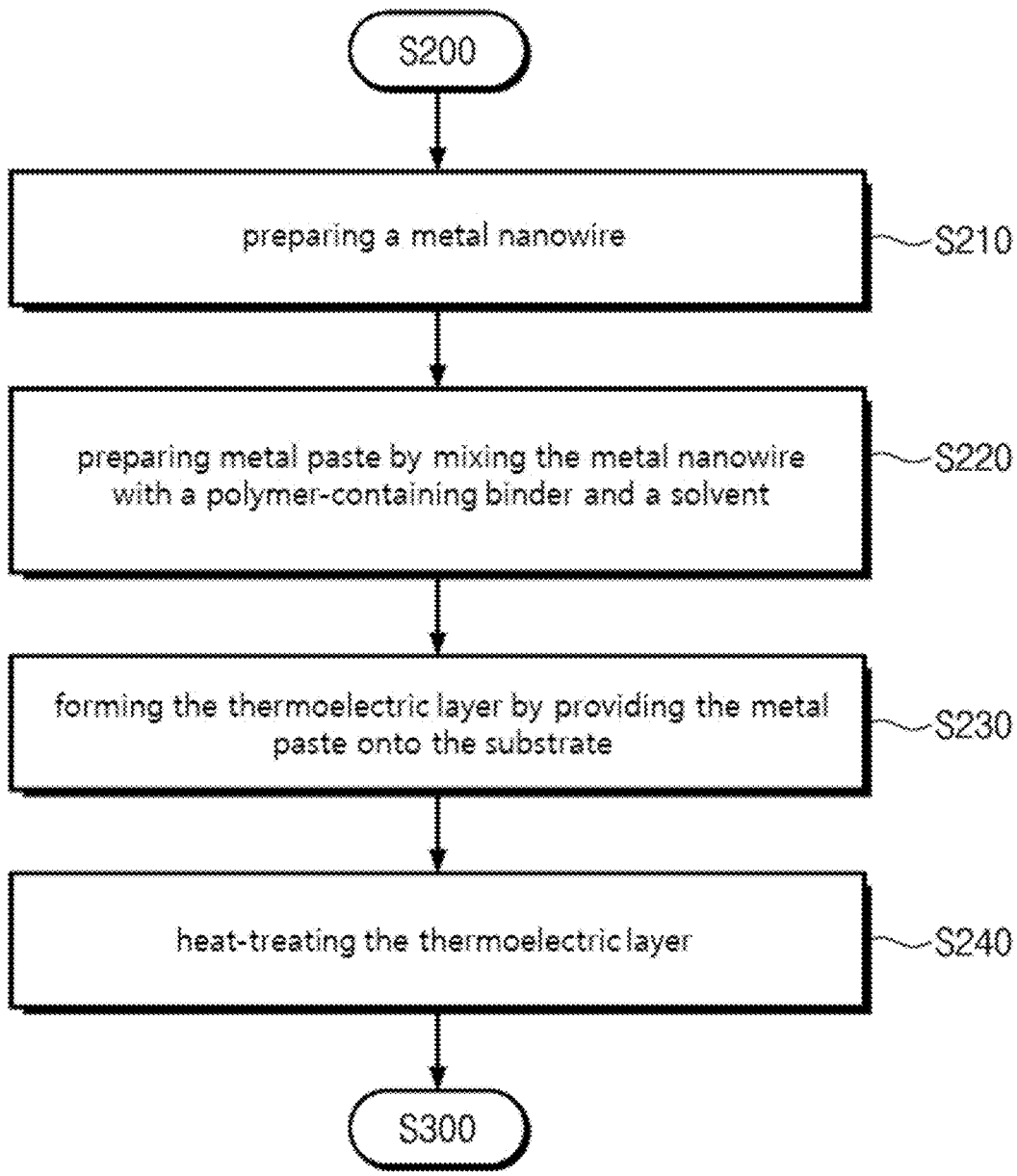
[FIG. 3]

[FIG. 4]
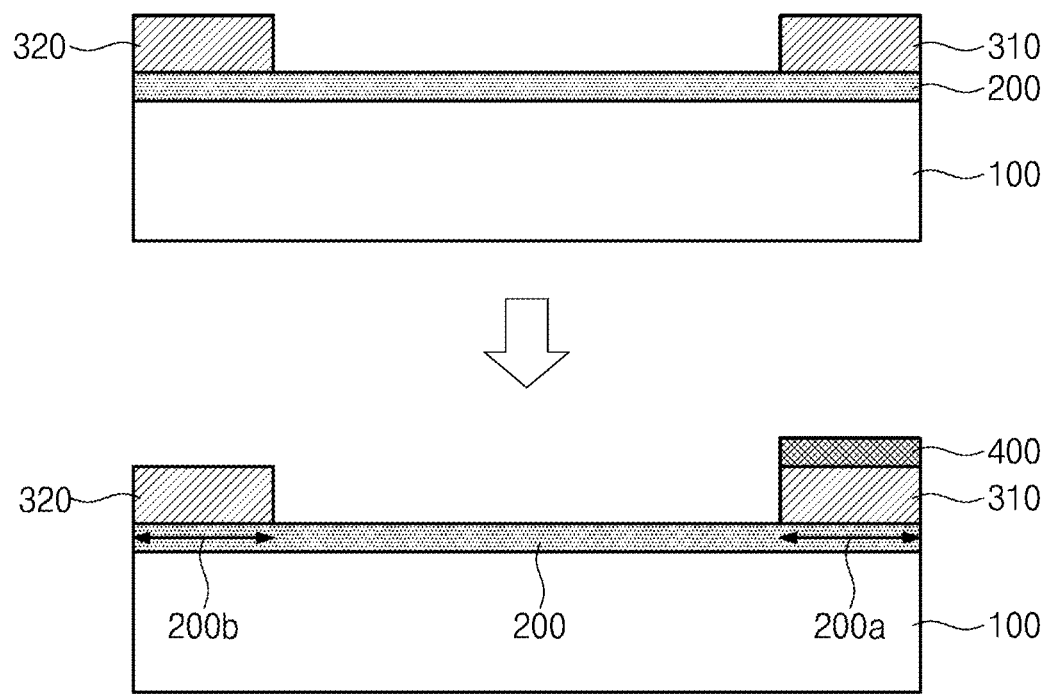

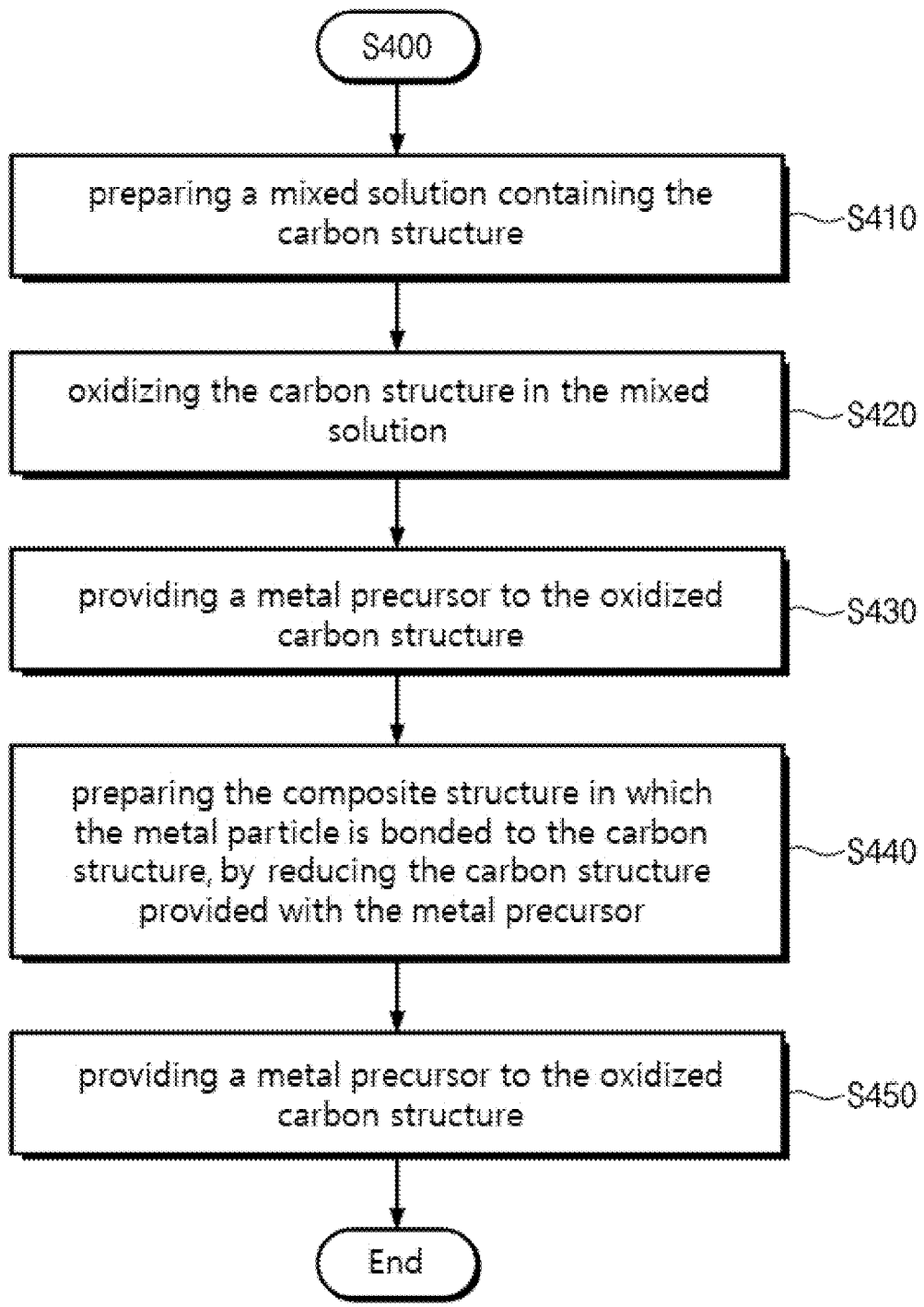
[FIG. 5]

[FIG. 6]
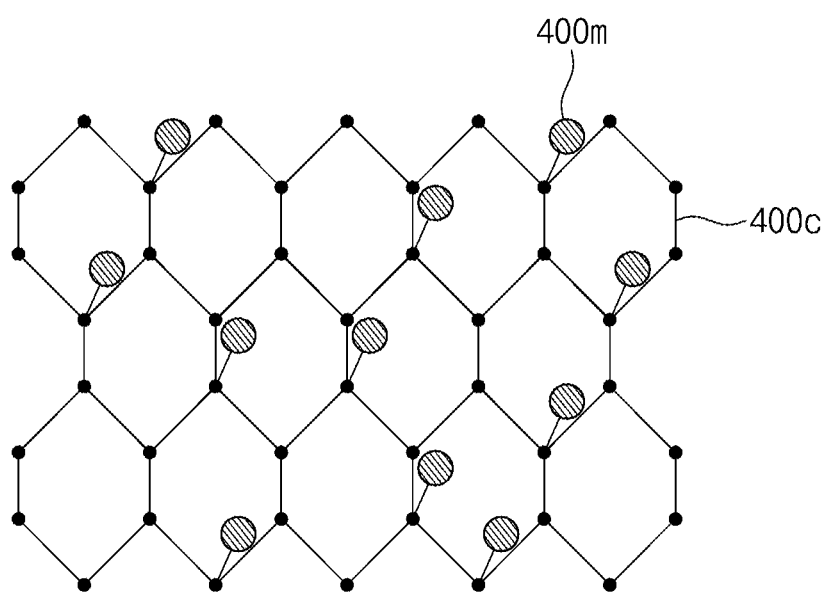

[FIG. 7]
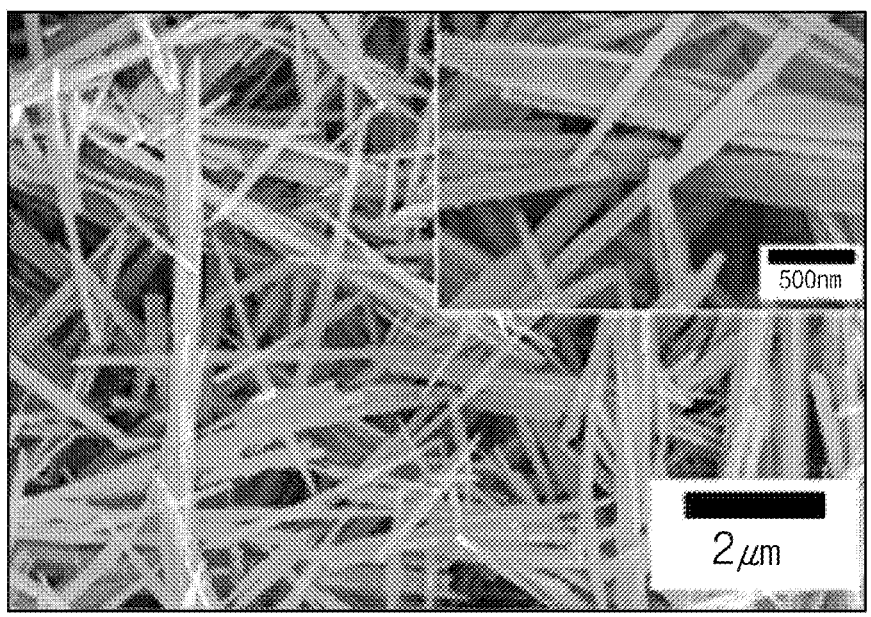

[FIG. 8]
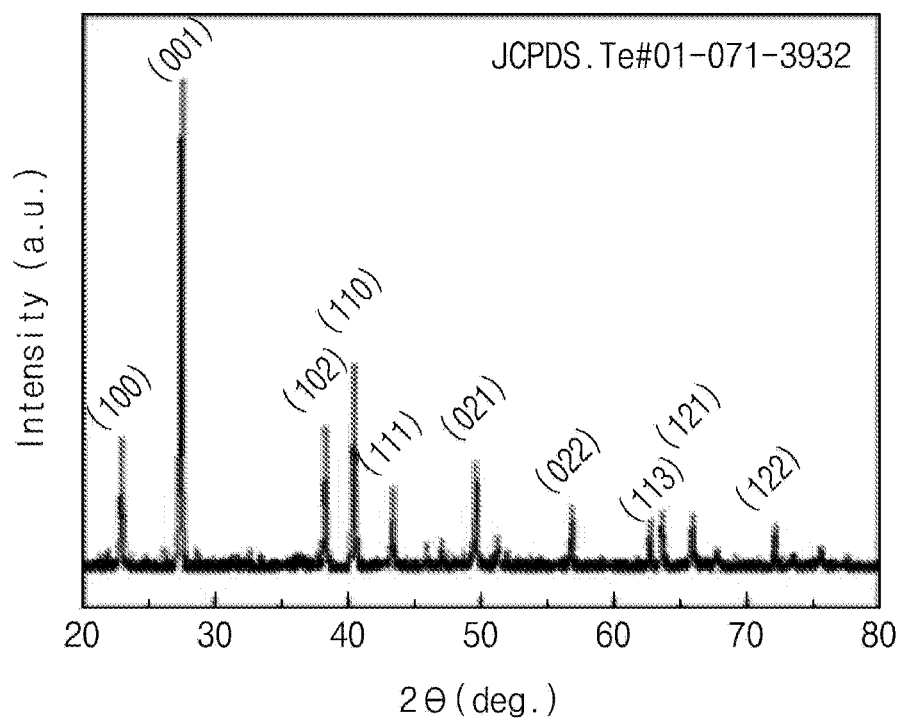
[FIG. 9]
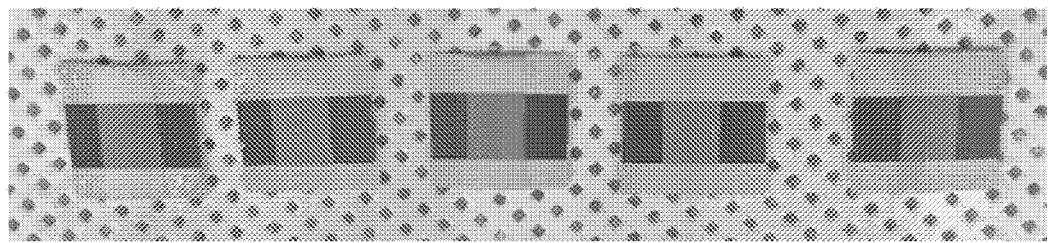

[FIG. 10]
(a)
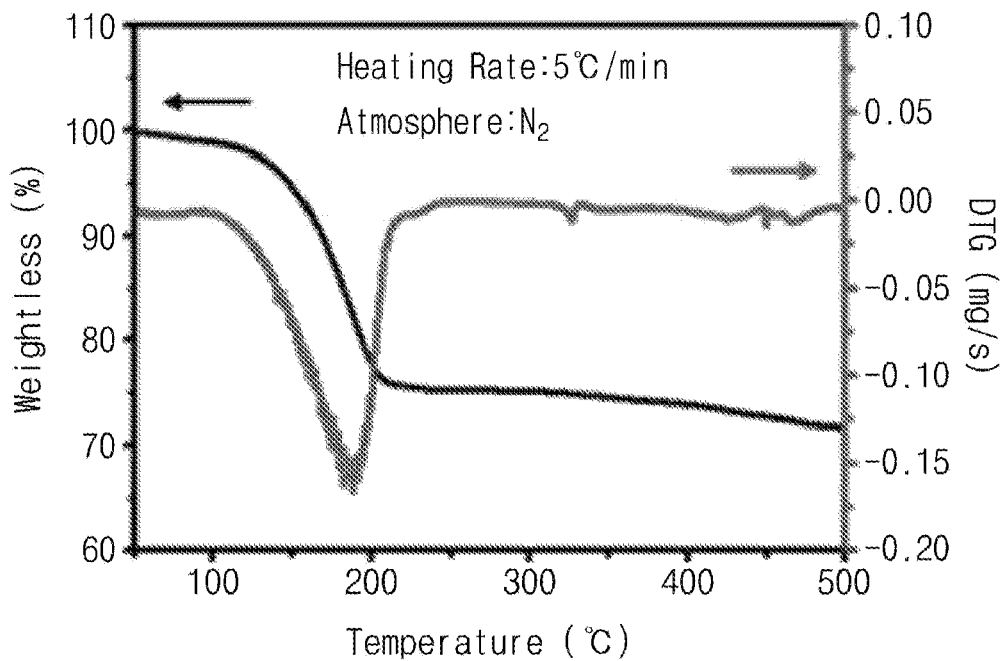
(b)
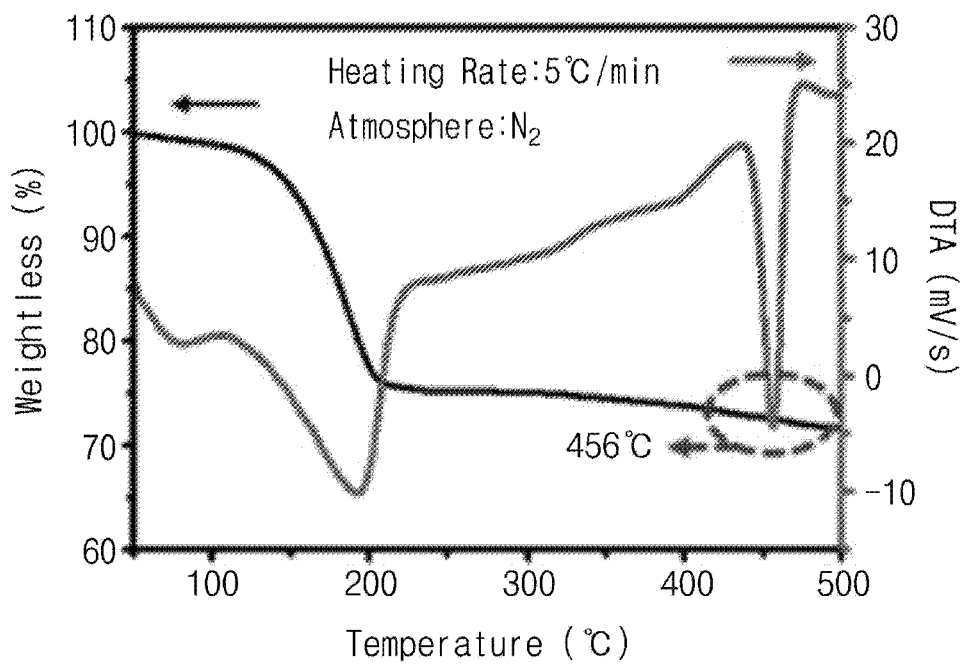

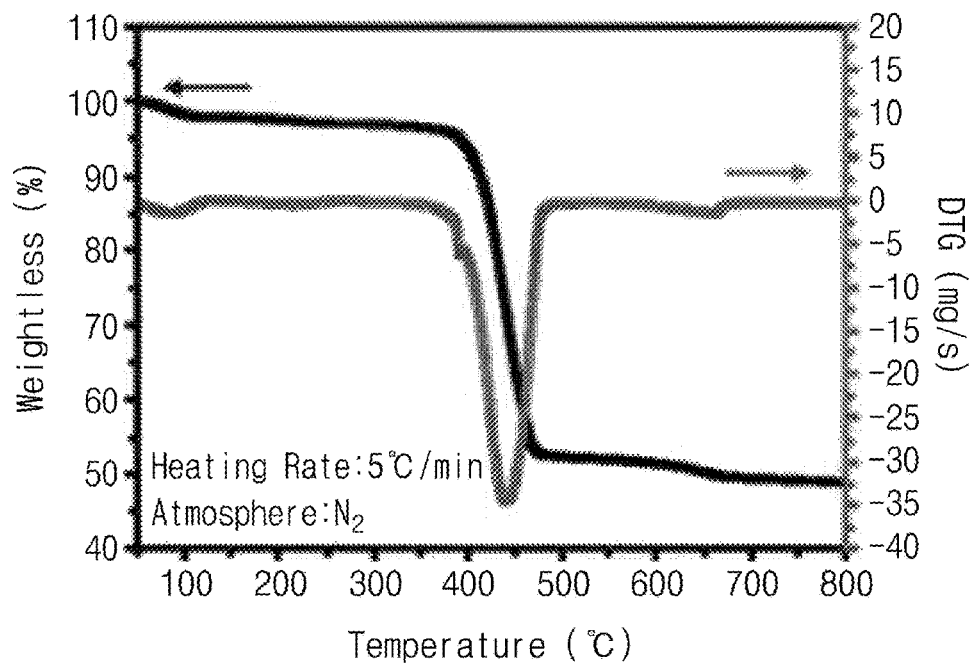
[FIG. 11]

[FIG. 12]
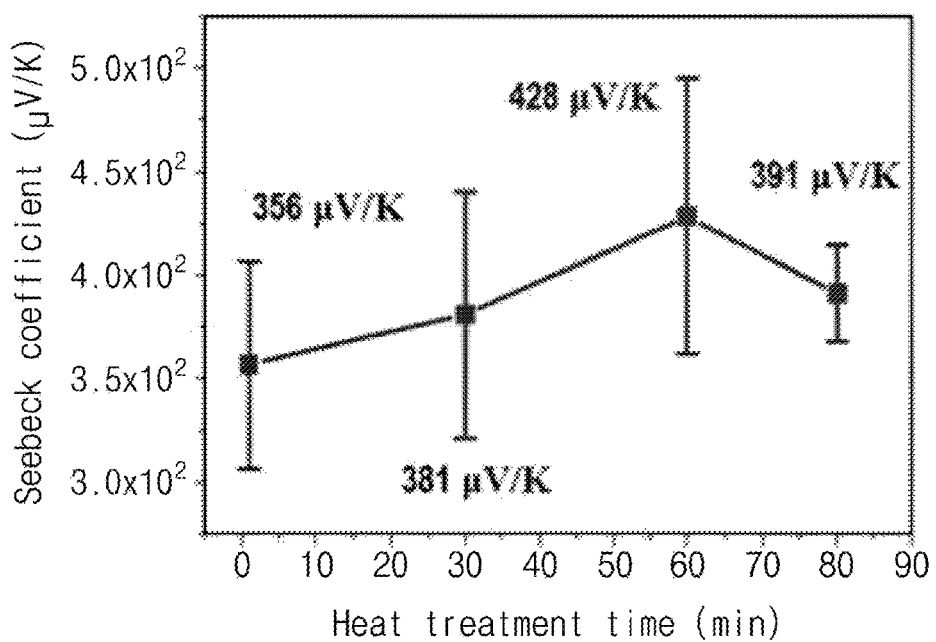

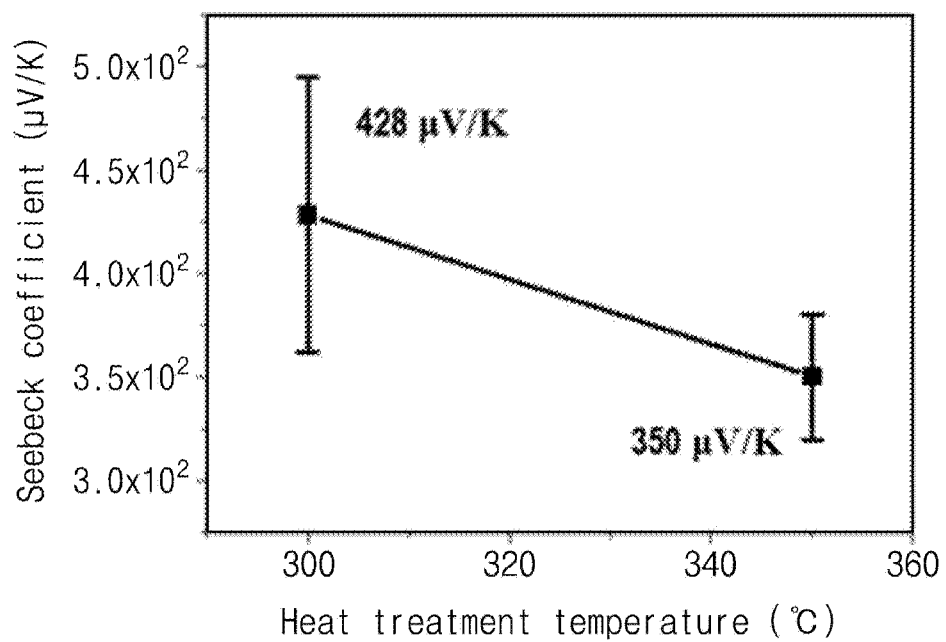
[FIG. 13]

[FIG. 14]
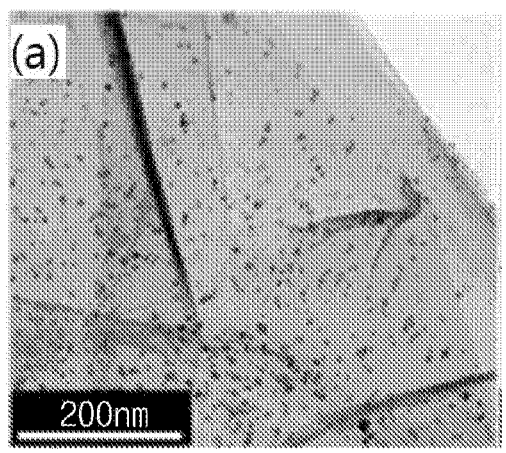
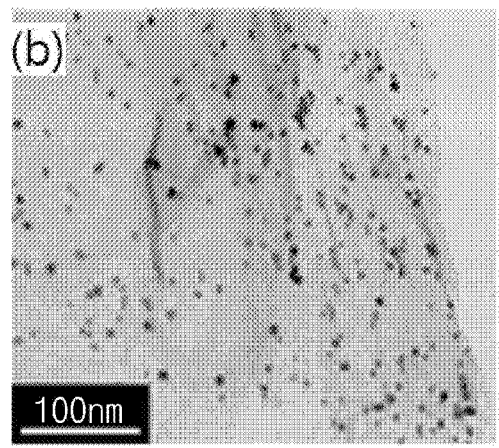

[FIG. 15]
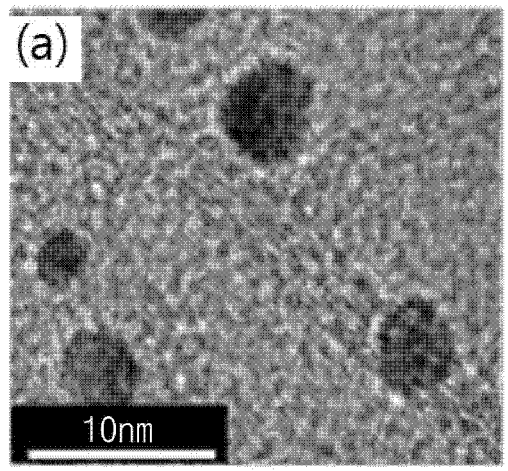
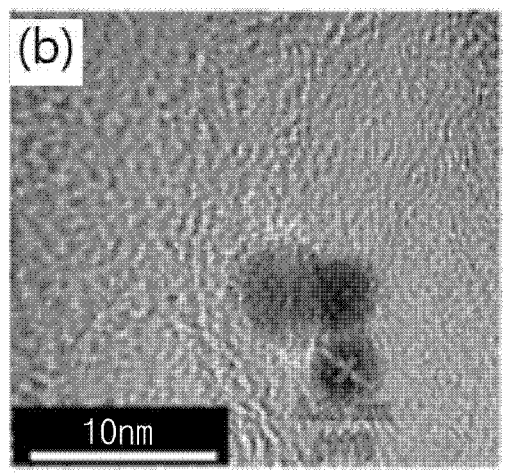

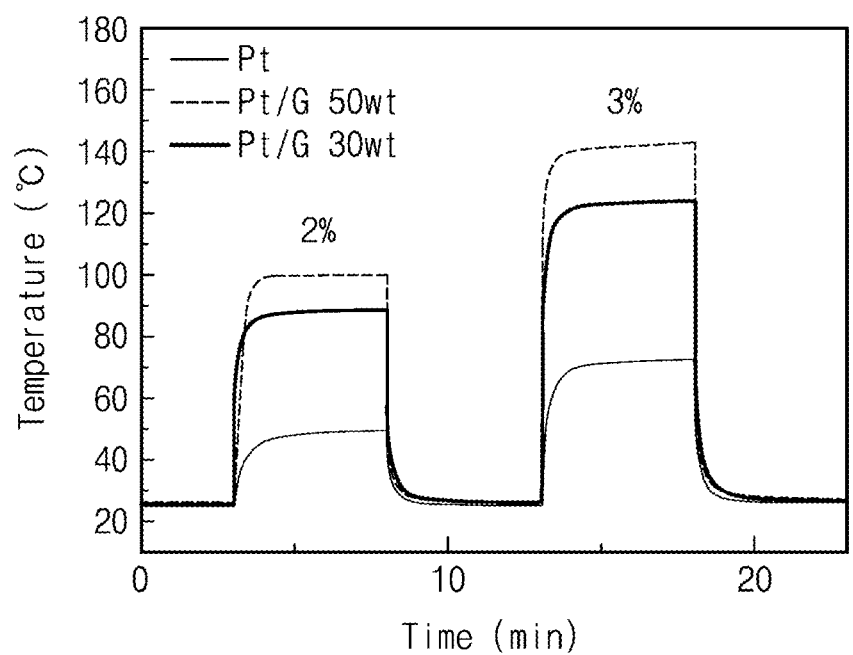

【FIG. 17】
(a)
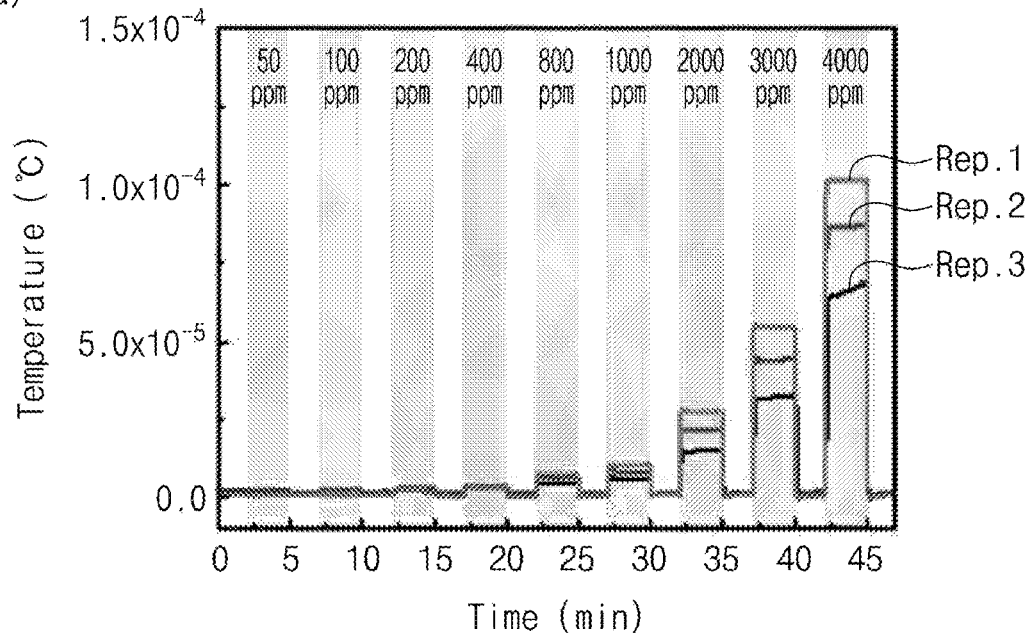
(b)
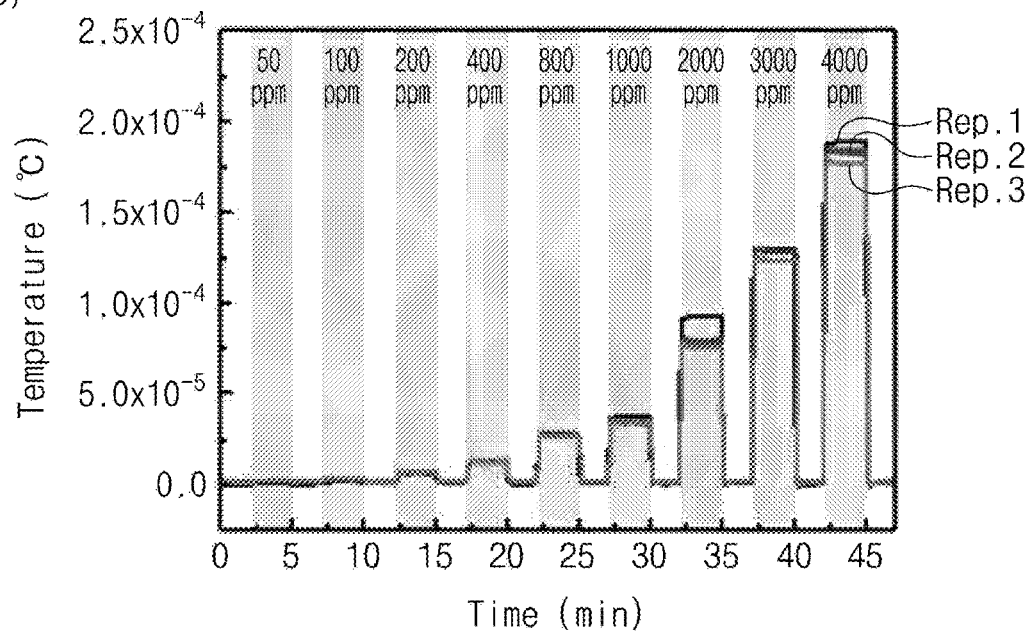

[FIG. 18A]
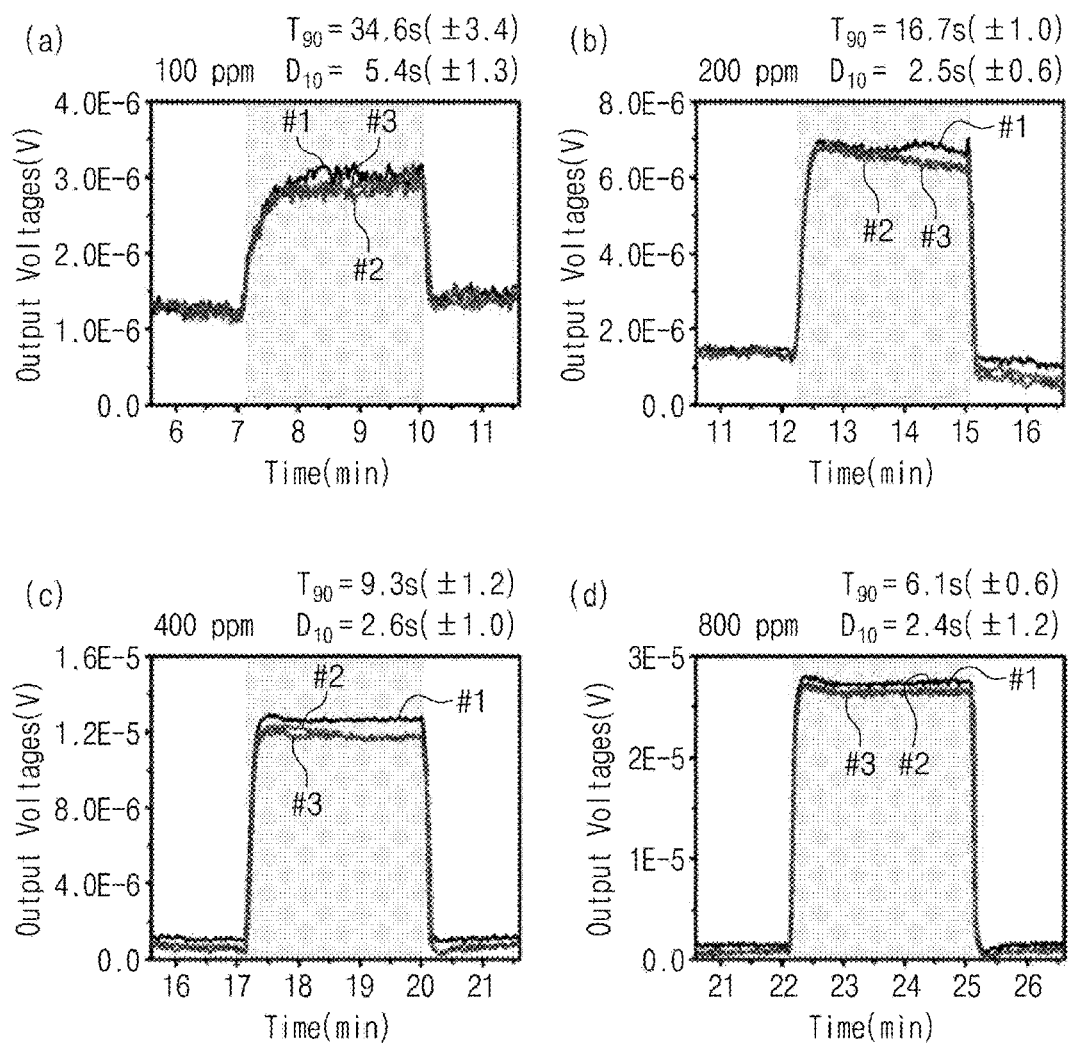

[FIG. 18B]
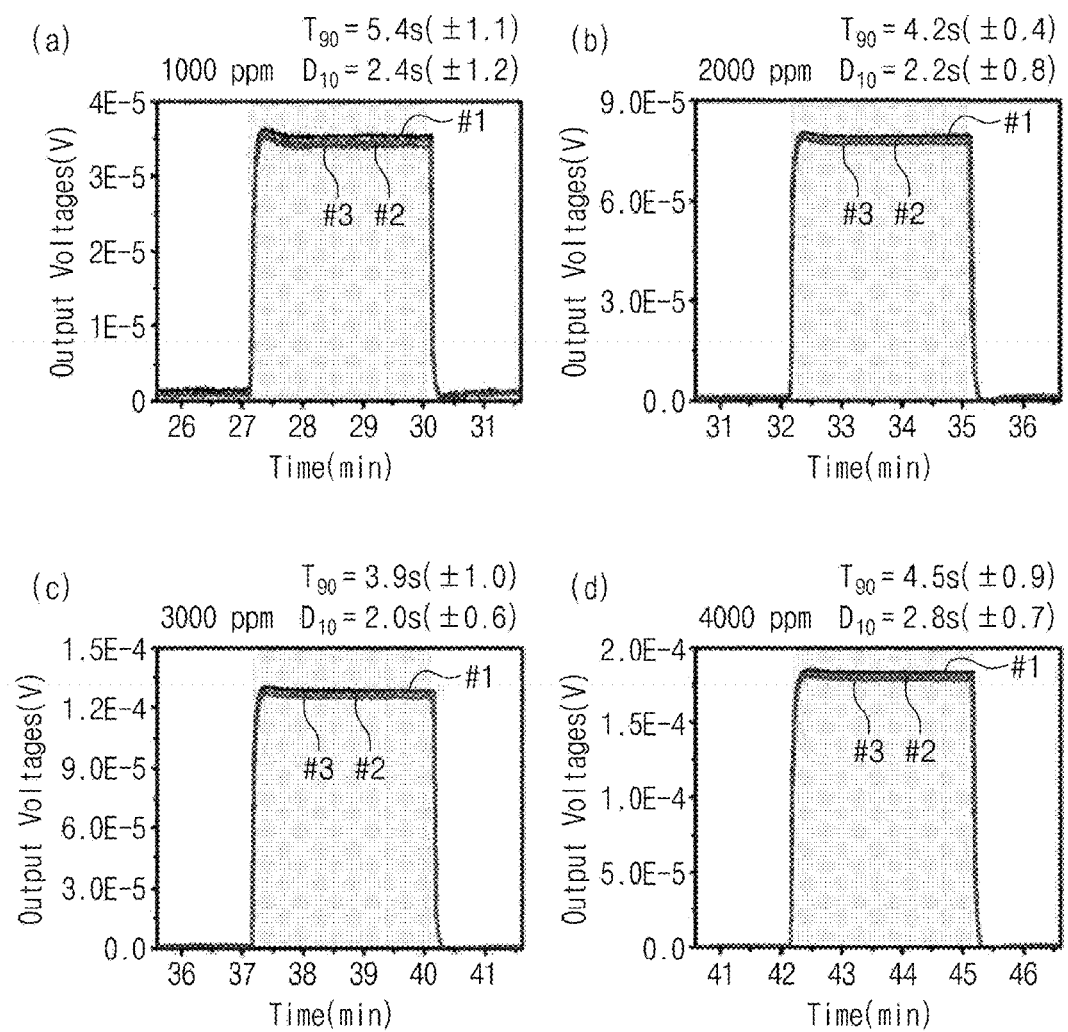

【FIG. 19】
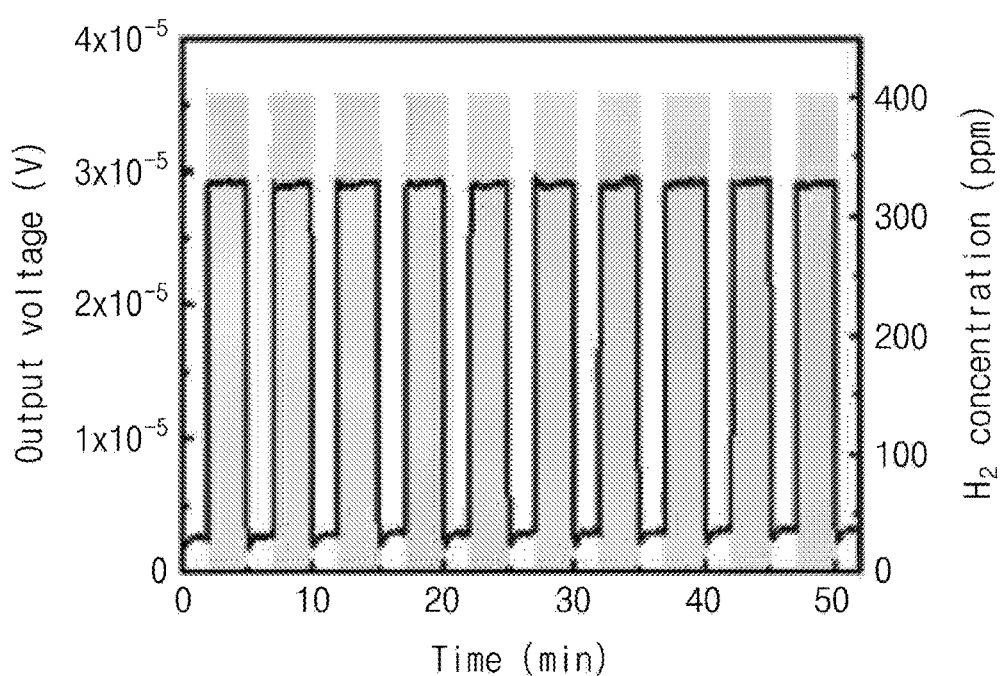

GAS SENSOR COMPRISING COMPOSITE STRUCTURE INCLUDING GRAPHENE AND METAL PARTICLE BONDED TO EACH OTHER AND METHOD FOR MANUFACTURING SAME

TECHNICAL FIELD

The present invention relates to a gas sensor and a method for manufacturing the same, and more particularly, to a gas sensor using thermoelectric properties and a method for manufacturing the same.

BACKGROUND ART

In general, a gas sensor identifies gas molecules by using adsorption reaction properties when the gas molecules touch a solid surface. In other words, the gas sensor operates based on the principle of measuring the amount of harmful gas by using the properties in which the electrical conductivity varies according to the degree of adsorption of the gas molecules. The gas sensor are mainly used for early detection of flammable or toxic gas to respond quickly. Numerous gas sensors using various detection techniques have been developed, and the gas sensor may be classified into an electrochemical type, a catalytic combustion type, a solid electrolyte type, a semiconductor type according to the detection principle.

In particular, although hydrogen gas is in much spotlight as an eco-friendly energy resource that may replace fossil fuels in the future, more precise and complete management and processing are required because hydrogen may explode caused by a small spark or heat and sunlight in an environment where hydrogen gas having a high concentration is mixed. Hydrogen gas has a wide explosive concentration range between 4% and 75% under normal circumstances. Accordingly, a hydrogen sensor can prevent hydrogen from being leaked when an accurate and fast measurement is available in the range excluding the explosive range, that is, the range within the hydrogen gas range of 4% or less, and the hydrogen sensor can be applied to a wider range when there is no effect from nitrogen, oxygen and water vapor (including humidity) present in the atmosphere or from the temperature, or when the effect is slight as possible. In addition, a commercialization may be substantially possible only when the hydrogen sensor has the very low power consumption and the compact size as well as the price competitiveness such that the hydrogen sensor is applied in the field of Internet of things (IoT) in the future. Hydrogen sensors using various principles have been developed so far.

In general, hydrogen sensors using contact combustion type, hot wire type, thermoelectric type, semiconductor type, electrochemical type, and metal absorption type schemes have been researched. Each operation scheme has advantages and disadvantages, however, a semiconductor type or thermoelectric type having a low power consumption, a compact size and a simple measurement is spotlighted as a next generation hydrogen sensor. However, the semiconductor type has low sensitivity due to a low reactivity with physically stable hydrogen gas at a surface of a semiconductor material. In the case of the thermoelectric type, sufficient researches have not been conducted and there is no commercial product so far.

To solve the above conventional problems, various technologies related to the hydrogen gas sensor have been developed. For example, Korean Unexamined Patent Publication No. 10-2011-0123022 (Application No.: 10-2010-0042437. Applicant: Industry-Academic Cooperation Foundation of the University of Seoul) discloses a hydrogen sensor and a method for manufacturing the same, the hydrogen sensor including: a silicon substrate, an insulating layer deposited on a surface of the substrate, A heater and an electrode formed on the insulating layer, a protective layer formed on the heater and the insulating layer where the heater is not formed to insulate between the heater and the electrode, and a catalyst layer connected between the electrodes on the protective layer.

Further, various technologies for forming fine patterns have been continuously researched and developed.

(Patent Document) Korean Unexamined Patent Publication No. 10-2011-0123022

DISCLOSURE

Technical Problem

The present invention provides a gas sensor having improved thermoelectric efficiency and a method for manufacturing the same.

The present invention further provides a gas sensor having improved thermal conductivity and a method for manufacturing the same.

The present invention still further provides a gas sensor manufactured with low costs and a method for manufacturing the same.

The present invention still further provides a gas sensor having improved stability of a catalyst layer and a method for manufacturing the same.

The present invention still further provides a gas sensor having high reliability and a method for manufacturing the same.

The present invention still further provides a gas sensor having high sensitivity and a method for manufacturing the same.

The technical problems to be solved by the present invention are not limited thereto.

Technical Solution

In order to solve the above-mentioned technical problems, the present invention provides a gas sensor.

According to one embodiment, the gas sensor includes: a substrate; a thermoelectric layer disposed on the substrate and including a metal nanowire; a first electrode and a second electrode spaced apart from each other on the thermoelectric layer; and a catalyst layer disposed on the first electrode and having a composite structure in which a metal particle is bonded to a carbon structure.

According to one embodiment, the catalyst layer may react with target gas, in which heat may be generated in the catalyst layer after the catalyst layer reacts with the target gas; the generated heat may cause a temperature difference between a first area of the thermoelectric layer in which the first electrode is disposed and a second area of the thermoelectric layer in which the second electrode is disposed; and the temperature difference between the first and second areas may cause a potential difference between the first area and the second area.

According to one embodiment, a concentration of the metal nanowire included in the thermoelectric layer may be greater than 60 wt % and less than 85 wt %.

According to one embodiment, the metal nanowire may include at least one of a tellurium nanowire, a BixTey nanowire, a BixSey nanowire, an SbxTey nanowire, and a PbTe1-xSex nanowire (x>0, y>0).

According to one embodiment, the ratio by weight (wt %) between the carbon structure and the metal particle may be 1:1.

According to one embodiment, the carbon structure may include graphene and the metal particle may include a platinum particle.

According to one embodiment, the carbon structure and the metal particle may form a covalent bond to each other.

According to one embodiment, in the gas sensor, the first electrode and the second electrode may be positioned at a same level based on a top surface of the substrate.

In order to solve the above-mentioned technical problems, the present invention provides a method for manufacturing a gas sensor.

According to one embodiment, the method for manufacturing a gas sensor includes: preparing a substrate; forming a thermoelectric layer including a metal nanowire on the substrate; forming a first electrode and a second electrode spaced apart from each other on the thermoelectric layer; and forming a catalyst layer having a composite structure in which a metal particle is bonded to a carbon structure on the first electrode.

According to one embodiment, the step of forming the thermoelectric layer may include: preparing the metal nanowire; preparing metal paste by mixing the metal nanowire with a polymer-containing binder and a solvent; forming the thermoelectric layer by providing the metal paste onto the substrate; and heat-treating the thermoelectric layer.

According to one embodiment, in the method for manufacturing a gas sensor, at least some of the metal nanowires in the thermoelectric layer may be melted or vaporized due to the heat treating, so that the metal nanowires may be networked.

According to one embodiment, the thermoelectric layer may be heat-treated at a temperature of 300° C. for more than 50 minutes and less than 70 minutes.

According to one embodiment, the binder may include PVP and the solvent may include at least one of DEG and DEGBE.

According to one embodiment, the forming of the catalyst layer may include: preparing a mixed solution containing the carbon structure; oxidizing the carbon structure in the mixed solution; providing a metal precursor to the oxidized carbon structure; preparing the composite structure in which the metal particle is bonded to the carbon structure, by reducing the carbon structure provided with the metal precursor; and providing the composite structure onto the first electrode.

Advantageous Effects

The gas sensor according to the embodiments of the present invention includes: a substrate; a thermoelectric layer disposed on the substrate and including a metal nanowire; a first electrode and a second electrode spaced apart from each other on the thermoelectric layer; and a catalyst layer disposed on the first electrode and having a composite structure in which a metal particle is bonded to a carbon structure. Accordingly, the catalyst layer may have the improved adhesion with the first electrode and thermal conductivity, so that the target gas can be easily sensed even at a high temperature.

In addition, the manufacturing process of the composite structure may be controlled such that the ratio by weight (wt %) between the carbon structure and the metal particle is 1:1. Accordingly, a gas sensor, which has a high response speed, high efficiency and high sensitivity, and a method for manufacturing the same may be provided.

DESCRIPTION OF DRAWINGS

FIG. 1 is a flow chart for explaining a method for manufacturing a gas sensor according to the embodiment of the present invention.

FIG. 2 is a view showing a process of manufacturing a thermoelectric layer during manufacturing the gas sensor according to the embodiment of the present invention.

FIG. 3 is a flowchart explaining a step of forming a thermoelectric layer, in detail, in the method for manufacturing the gas sensor according to the embodiment of the present invention.

FIG. 4 a view showing a process of manufacturing an electrode and a catalyst layer during manufacturing the gas sensor according to an embodiment of the present invention.

FIG. 5 is a flowchart explaining a step of forming a catalyst layer, in detail, in the method for manufacturing the gas sensor according to the embodiment of the present invention.

FIG. 6 is a view showing a composite structure, in detail, included in the catalyst layer of the gas sensor according to the embodiment of the present invention.

FIG. 7 is a photograph obtained by photographing a thermoelectric layer included in the gas sensor according to the embodiment of the present invention.

FIG. 8 is a graph obtained by analyzing the thermoelectric layer included in the gas sensor according to an embodiment of the present invention.

FIG. 9 is a photograph obtained by photographing a structure of the gas sensor according to the embodiment of the present invention.

FIG. 10 is a graph showing the thermal analysis properties of metal paste used for manufacturing the thermoelectric layer included in the gas sensor according to the embodiment of the present invention.

FIG. 11 is a graph showing the thermal analysis properties of PVP used for manufacturing the thermoelectric layer included in the gas sensor according to the embodiment of the present invention.

FIGS. 12 and 13 are graphs showing the thermoelectric properties of the thermoelectric layer included in the gas sensor according to the embodiment of the present invention.

FIGS. 14 and 15 are photographs obtained by photographing the composite structure of the catalyst layer included in the gas sensor according to the embodiment of the present invention.

FIG. 16 is a graph showing the properties of the catalyst layer included in the gas sensor according to the embodiment of the present invention.

FIG. 17 is a graph for comparing changes in the properties upon the heat treatment of the gas sensor according to the embodiment of the present invention.

FIGS. 18A and 18B are graphs showing the properties according to the hydrogen concentration provided to the gas sensor according to the embodiment of the present invention.

FIG. 19 is a graph showing the reliability of the gas sensor according to the embodiment of the present invention.

BEST MODE

Mode for Invention

Hereinafter, preferred embodiments of the present invention will be described in detail with reference to the accompanying drawings. However, the technical idea of the present invention is not limited to the exemplary embodiments described herein and may be embodied in other forms. Further, the embodiments disclosed thoroughly and completely herein may be provided such that the idea of the present invention can be fully understood by those skilled in the art.

In the specification, when one component is mentioned as being on another component, it signifies that the one component may be placed directly on another component or a third component may be interposed therebetween. Further, in drawings, thicknesses of films and regions may be exaggerated to effectively describe the technology of the present invention.

In addition, although terms such as first, second and third are used to describe various components in various embodiments of the present specification, the components should not be limited by the terms. The above terms are used merely to distinguish one component from another. Accordingly, a first component referred to in one embodiment may be referred to as a second component in another embodiment. Each embodiment described and illustrated herein may also include a complementary embodiment. In addition, the term "and/or" is used herein to include at least one of the components listed before and after the term.

The singular expression herein includes a plural expression unless the context clearly specifies otherwise. In addition, it should be understood that the term such as "include" or "have" herein is intended to designate the presence of feature, number, step, component, or a combination thereof recited in the specification, and does not preclude the possibility of the presence or addition of one or more other features, numbers, steps, components, or combinations thereof. In addition, the term "connection" is used herein to include both indirectly connecting a plurality of components and directly connecting the components.

Further, in the following description of the embodiments of the present invention, the detailed description of known functions and configurations incorporated herein will be omitted when it possibly makes the subject matter of the present invention unclear unnecessarily.

FIG. 1 is a flow chart for explaining a method for manufacturing a gas sensor according to the embodiment of the present invention. FIG. 2 is a view showing a process of manufacturing a thermoelectric layer during manufacturing the gas sensor according to the embodiment of the present invention.

Referring to FIGS. 1 and 2, a substrate 100 is prepared (S100). According to one embodiment, the substrate 100 may be a silicon oxide substrate. Alternatively, in contrast, the substrate 100 may be a semiconductor substrate, a compound semiconductor substrate, a glass substrate, a plastic substrate (such as PI substrate), or a metal substrate.

A thermoelectric layer 200 may be famed on the substrate 100 (S200). The thermoelectric layer 200 may generate electric signals by receiving heat generated by a catalyst layer 400 described below and reacting with target gas.

According to one embodiment, the thermoelectric layer 200 may include metal nanowires. For example, the metal nanowire may be a tellurium nanowire. For another example, the metal nanowire may include at least one of a BixSey nanowire, a BixSey nanowire, an SbxTey nanowire, and a PbTe1-xSex nanowire (x>0, y>0).

According to one embodiment, a concentration of the metal nanowire included in the thermoelectric layer 200 may be greater than 60 wt % and less than 85 wt %. For example, when the metal nanowire is a tellurium nanowire, the thermoelectric layer 200 may include a tellurium nanowire having a concentration of 75 wt %. In contrast, when the thermoelectric layer 200 includes a tellurium nanowire having a concentration of 60 wt % or less, the thermoelectric layer 200 may have cracks. In addition, when the thermoelectric layer 200 includes a tellurium nanowire having a concentration of 85 wt % or more, the thermoelectric layer 200 may be separated from the substrate 100.

Hereinafter, the method for manufacturing the thermoelectric layer 200 will be described in detail with reference to FIG. 3.

FIG. 3 is a flowchart explaining a step of forming a thermoelectric layer, in detail, in the method for manufacturing the gas sensor according to the embodiment of the present invention.

Referring to FIGS. 2 and 3, step S200 of forming the thermoelectric layer 200 may include preparing the metal nanowire (S210); preparing metal paste (S220); forming the thermoelectric layer 200 by providing the metal paste onto the substrate 100 (S230); and heat-treating the thermoelectric layer 200 (S240). Hereinafter, for convenience of description, it will be assumed that the metal nanowire is a tellurium nanowire.

According to one embodiment, step S210 of preparing the metal nanowire may include mixing metal oxide with a solvent; and reducing the metal oxide mixed with the solvent. For example, the metal oxide may be tellurium oxide. The solvent may be ethylene glycol. For example, a reducing agent for reducing the metal oxide mixed with the solvent may be hydroxyl amine.

Specifically, in order to prepare the tellurium nanowire, tellurium oxide having a capacity of 5 g may be mixed with ethylene glycol having a capacity of 250 ml, and stirred at a temperature of 160° C. for 2 hours. Then, hydroxyl amine having a concentration of 50 wt % and a capacity of 5 ml was added and stirred for 1 hour, so that the tellurium nanowire may be prepared.

The metal paste may be prepared by mixing the metal nanowire with a binder and a solvent. According to one embodiment, the binder may include a polymer. For example, the polymer may be polyvinylpyrrolidone (PVP). For another example, the polymer may be polyacrylonitrile (PAN), poly(vinyl acetate) (PVAc), polyvinyl butyral (PVB), poly(vinyl alcohol) (PVA), polyethylene oxide (PEO), and the like. For example, the solvent may include at least one of diethylene glycol (DEG) and diethylene glycol butyl ether (DEGBE). For another example, the solvent may include at least one of methanol, ethanol, propanol, isopropanol, butanol, 2-butanol, pentanol, 2-ethylhexy alcohol, cyclohexanol, phenol, ethylene glycol, 1,3-butanediol, 1,4-butanediol, and glycerol. For example, when the solvent includes DEG and DEGBE and the binder includes PVP, DEG, DEGBE and PVP may have the ratio of 1:0.8:0.2 by weight (wt %).

According to one embodiment, the thermoelectric layer 200 may be formed by providing the metal paste onto the substrate 100 by using a tape casting scheme. When the thermoelectric layer 200 is formed by using the metal paste through the tape casting scheme, the mass production and the control of a film shape can be easily performed.

In step S240 of heat-treating the thermoelectric layer 200, the metal nanowires in the thermoelectric layer 200 may be networked. Specifically, when the thermoelectric layer 200 is heat-treated, at least some of the metal nanowires in the thermoelectric layer 200 may be melted or vaporized. Accordingly, the contact between the metal nanowires may be improved, so that the metal nanowires may be networked.

According to one embodiment, the thermoelectric layer 200 may be heat-treated at a temperature of 300° C. for more than 50 minutes and less than 70 minutes. For example, the thermoelectric layer 200 may be heat-treated at the temperature of 300° C. for 60 minutes. Accordingly, the thermoelectric layer 200 may have a maximum value of the Seebeck coefficient. In contrast, when the thermoelectric layer 200 is heat-treated at the temperature of 300° C. for 50 minutes or less, the metal nanowires in the thermoelectric layer 200 may be not sufficiently melted or vaporized, thereby deteriorating the thermoelectric properties of the thermoelectric layer 200. In addition, when the thermoelectric layer 200 is heat-treated at the temperature of 300° C. for 70 minutes or more, the metal nanowires in the thermoelectric layer 200 may be excessively melted or vaporized, thereby deteriorating the thermoelectric properties of the thermoelectric layer 200.

Next, a first electrode 310, a second electrode 320, and a catalyst layer disposed on the thermoelectric layer 200 will be described with reference to FIGS. 1, 4 and 5.

FIG. 4 a view showing a process of manufacturing an electrode and a catalyst layer during manufacturing the gas sensor according to the embodiment of the present invention.

Referring to FIGS. 1 and 4, the first electrode 310 and the second electrode 320 may be formed on the thermoelectric layer 200 (S300). The first electrode 310 and the second electrode 320 may be spaced apart from each other. According to one embodiment, the first electrode 310 and the second electrode 320 may include a metal. For example, the first electrode 310 and the second electrode 320 may include gold (Au).

According to one embodiment, the first electrode 310 and the second electrode 320 may be positioned at the same level based on a top surface of the substrate 100. In other words, the first electrode 310 and the second electrode 320 may be spaced apart from each other and disposed in parallel to each other on the thermoelectric layer 200. A catalyst layer 400 may be disposed on the first electrode 310. The catalyst layer 400 may be provided on the first electrode 310 and may not be provided on the second electrode 320.

The catalyst layer 400 may react with target gas. The catalyst layer 400 may generate heat after reacting with the target gas. Accordingly, a temperature difference may occur between a first area 200a and a second area 200b of the thermoelectric layer 200. According to one embodiment, the first area 200a may be an area in which the first electrode 310 is disposed on the thermoelectric layer 200. According to one embodiment, the second area 200b may be an area in which the second electrode 320 is disposed on the thermoelectric layer 200. Due to the temperature difference between the first area 200a and the second area 200b, a potential difference may be generated between the first area 200a and the second area 200b.

In other words, when the catalyst layer 400 reacts with the target gas, heat may be generated in the catalyst layer 400. When the catalyst layer 400 is disposed on the first electrode 310, the heat generated in the catalyst layer 400 may be transferred to the first area 200a through the first electrode 310. In contrast, since the catalyst layer 400 is not disposed on the second electrode 320, the second area 200b may have a lower temperature compared to the first area 200a. Accordingly, the temperature difference may be generated between the first area 200a and the second area 200b, and the temperature difference may cause a potential difference between the first area 200a and the second area 200b.

Hereinafter, the method for manufacturing the catalyst layer 400 will be described in detail with reference to FIG. 5, and the composite structure included in the catalyst layer 400 will be described with reference to FIG. 6.

FIG. 5 is a flowchart explaining a step of forming a catalyst layer, in detail, in the method for manufacturing the gas sensor according to the embodiment of the present invention.

Referring to FIG. 5, step S400 of forming the catalyst layer 400 may include: preparing a mixed solution containing the carbon structure 400c (S410); oxidizing the carbon structure 400c in the mixed solution (S420); providing a metal precursor 400m to the oxidized carbon structure 400c (S430); preparing the composite structure by reducing the carbon structure 400c provided with the metal precursor 400m (S440); and providing the composite structure onto the first electrode 310 (S450). According to one embodiment, the metal precursor 400m may be chloroplatinic acid hexahydrate (H2PtCl6.6H2O).

Specifically, for example, a mixed solution containing graphene, water, and ionic liquid may be prepared. The mixed solution may pass through a high pressure disperser, so that graphene in the mixed solution may be oxidized. Next, the mixed solution containing the oxidized graphene may be added with a chloroplatinic acid hexahydrate solution, refluxed, and then added with a reducing agent (such as NaBH4), so that the oxidized graphene provided with chloroplatinic acid hexahydrate may be reduced. Accordingly, the composite structure obtained by bonding platinum particles to graphene may be prepared. Then, the composite structure may be applied on the first electrode 310 to form the catalyst layer 400.

According to one embodiment, in step S400 of forming the catalyst layer 400, a heat treatment may be performed after the composite structure is provided onto the first electrode 310. Accordingly, the catalyst layer 400 may be stabilized. Unlike the above-described embodiment, when the catalyst layer 400 includes only the metal particles 400m, it may be difficult to perform the heat treatment process for stabilizing the catalyst layer 400 since the metal particles 400m aggregate at high temperature as described with reference to FIG. 3. However, in the catalyst layer 400 of the gas sensor according to the embodiments of the present invention, the metal particles 400m are bonded to the carbon structure 400c, so that the heat treatment process for stabilizing the catalyst layer 400 can be easily performed.

According to one embodiment, in the catalyst layer 400, the ratio by weight (wt %) between the carbon structure 400c and the metal particles 400m may be 1:1. To this end, the amounts of the metal precursor and the reducing agent may be controlled. For example, the amount of the metal precursor may be controlled after calculating the required mass ratio of platinum based on a graphene solution of 50 ml by 1 mg/ml; dividing the mass ratio of platinum by density (195/084 g/mol) to obtain the required number of moles; and multiplying a molecular weight value of H2PtCl6 (517.90 g/mol). For example, the amount of the reducing agent may be controlled by six times the equivalent of the amount of the precursor. In contrast, when the metal particles 400m has wt % higher than the carbon structure 400c in the catalyst layer 400, economic problems may occur due to the metal particles 400m having high costs.

FIG. 6 is a view showing a composite structure, in detail, included in catalyst layer of the gas sensor according to the embodiment of the present invention.

Referring to FIG. 6, the catalyst layer 400 may include a composite structure in which metal particles 400m are coupled to the carbon structure 400c. For example, the carbon structure may be graphene. For example, the metal particle may be a platinum (Pt) particle.

The metal particles 400m may generate heat after reacting with the target gas. For example, the target gas may be hydrogen gas. The carbon structure 400c may provide a strong bonding force between the composite structure and the first electrode 310. In other words, due to the carbon structure 400c, the metal particles 400m may be easily provided onto the first electrode 310. In addition, the carbon structure 400c may improve thermal conductivity such that the heat generated from the metal particles 400m is easily provided to the first electrode 310.

According to one embodiment, the ration by weight (wt %) between the carbon structure and the metal particles may be 1:1 in the catalyst layer 400. In contrast, when the wt % of the metal particles is higher than the carbon structure in the catalyst layer 400, economic problems may occur due to the metal particles having high costs.

The carbon structure 400c and the metal particles 400m may form a covalent bond to each other. Accordingly, the metal particles 400m may be strongly bonded to a surface of the carbon structure 400c.

When the metal particles 400m are not covalently bonded to the carbon structure 400c unlike the embodiment of the present invention, the metal particles 400m may aggregate with each other by the heat generated after the metal particles 400m react with the target gas. Accordingly, the reliability of a device may be degraded.

However, according to an embodiment of the present invention as described above, the metal particles 400m may be covalently bonded to the carbon structure 400c, so that the mutual aggregation in the high temperature environment may be minimized. Accordingly, a gas sensor having high reliability even in a high temperature environment can be provided.

The gas sensor according to the embodiments of the present invention may include: the substrate 100; the thermoelectric layer 200 disposed on the substrate 100 and including the metal nanowire; the first electrode 310 and the second electrode 320 spaced apart from each other on the thermoelectric layer 200; and the catalyst layer 400 disposed on the first electrode 310 and having the composite structure in which the metal particles 400m are bonded to the carbon structure 400c. Accordingly, the catalyst layer 400 may have the improved adhesion with the first electrode 310 and the improved thermal conductivity, and may easily sense the target gas even in the high temperature environment.

In addition, the manufacturing process of the composite structure may be controlled such that the ratio by weight (wt %) between the carbon structure 400c and the metal particles 400m is 1:1 in the catalyst layer 400. Accordingly, a gas sensor having a high response speed, high efficiency and high sensitivity, and a method for manufacturing the same may be provided.

Hereinafter, specific experimental examples and property evaluation results on the gas sensor according to the embodiments of the present invention will be described.

Manufacture of Gas Sensor According to Experimental Examples

After tellurium oxide having a capacity of 5 g was mixed with ethylene glycol having a capacity of 250 ml, and stirred for 2 hours at a temperature of 160° C., hydroxyl amine having a concentration of 50 wt % and a capacity of 5 ml was added and stirred for 1 hour, so that a tellurium nanowire was prepared.

In addition, the prepared tellurium nanowire was mixed with a solvent containing DEG, DEGBE and PVP at the ratio of 1:0.8:0.2, in which the tellurium nanowire was mixed to have a concentration of 75 wt % in the entire solution, so that tellurium paste was prepared.

a silicon oxide substrate was coated with the prepared tellurium paste having a width of 6 mm and a height of 12 mm by using a tape casting scheme, and two gold (Au) electrodes were disposed to be spaced apart from each other on the coating tellurium paste by using a sputtering scheme.

Then, a water solution dispersed therein with graphene having a concentration of 10 wt % was diluted to prepare a solution of 1 mg/ml, added with a solution of chloroplatinic acid hexahydrate having a capacity of 88 mg, and refluxed at 70° C. for 10 minutes at a speed of 830 rpm. Next, the refluxed solution was added with a solution obtained by mixing NaBH4 having a capacity of 32 mg and distilled water having a capacity of 20 ml at a rate of 1 ml/min, and spun for 5 minutes at a rate of 1000 rpm through a centrifuge, so that a catalyst was prepared.

The prepared catalyst was deposited on one of the two gold electrodes, and thus a final gas sensor was manufactured.

FIG. 7 is a photograph obtained by photographing a thermoelectric layer included in the gas sensor according to the embodiment of the present invention.

Referring to FIG. 7, a thermoelectric layer included in the gas sensor according to the embodiment was photographed by a field emission scanning electron microscopy (FE-SEM). As shown in FIG. 7, it was confirmed that a thermoelectric layer containing tellurium nanowires having a diameter of 173.78 nm (±66 nm) and a length of 2.7 μm (±1.1 μm) was formed on the substrate.

FIG. 8 is a graph obtained by analyzing the thermoelectric layer included in the gas sensor according to an embodiment of the present invention.

Referring to FIG. 8, the thermoelectric layer included in the gas sensor according to the embodiment was analyzed by X-ray diffraction (XRD). As shown in FIG. 8, it was confirmed that the thermoelectric layer was formed therein with a phase of tellurium (JCPDS No. 01-071-3932). In addition, it was confirmed that the tellurium having high purity and free of impurities was formed because a peak related to tellurium oxide was not observed in the thermoelectric layer.

As shown in FIGS. 7 and 8, in the gas sensor according to the embodiments of the present invention, it can be seen that a nanowire formed of a single tellurium phase on the substrate is formed as the thermoelectric layer.

In addition, Table 1 summarizes the results as follows on forming the thermoelectric layer according to a wt % concentration and a drying condition of the tellurium nanowire contained in the thermoelectric layer included in the gas sensor according to the embodiment.

TABLE 1

| Tellurium nanowire wt % | Drying condition | Thermoelectric layer |
| --- | --- | --- |
| 50 wt % | Drying at 60° C. for 12 h | Non-uniform layer was formed |
| 60 wt % | Drying at 60° C. for 12 h | Cracks were generated |
| 75 wt % | Drying at 60° C. for 12 h | Cracks were generated |
| 75 wt % | Room temperature for 24 h | Uniform layer was formed |
| 85 wt % | Room temperature for 24 h | Separate from the substrate |

As shown in Table 1, it can be seen that the uniform thermoelectric layer may easily formed when the thermoelectric layer of the gas sensor according to the embodiment includes the tellurium nanowire at a concentration of more than 60 wt % and less than 85 wt %.

FIG. 9 is a photograph obtained by photographing a structure of the gas sensor according to the embodiment of the present invention.

Referring to FIG. 9, a structure of the gas sensor according to the embodiment was photographed in which a state before depositing the catalyst layer was generally photographed. As shown in FIG. 9, in the gas sensor according to the embodiment, it was confirmed that the thermoelectric layer including the tellurium nanowires was formed on the silicon oxide substrate, and two gold (Au) electrodes were formed spaced apart from each other on the thermoelectric layer.

FIG. 10 is a graph showing the thermal analysis properties of metal paste used for manufacturing the thermoelectric layer included in the gas sensor according to the embodiment of the present invention.

FIGS. 10(a) and 10(b) show the metal paste used for preparing the thermoelectric layer included in the gas sensor according to the embodiment, by using differential thermal analysis (TG-DTA). As shown in FIGS. 10(a) and 10(b), in the metal paste used for preparing the thermoelectric layer included in the gas sensor according to the embodiment, it was confirmed that DTG (mg/s) rapidly fluctuated at 200° C. and DTA (mV/s) rapidly fluctuated at 456° C. This is because the solution used for preparing the metal paste is actively dried at 200° C., and the weight loss of PVP occurs at 400° C. In addition, it can be seen that the weight loss occurs in the metal paste from 300° C. or higher, because small amounts of atoms were vaporized on the surface of the tellurium nanowire due to the high evaporation pressure of the tellurium nanowire.

FIG. 11 is a graph showing the thermal analysis properties of PVP used for manufacturing the thermoelectric layer included in the gas sensor according to the embodiment of the present invention.

Referring to FIG. 11, the PVP used for preparing the thermoelectric layer included in the gas sensor according to the embodiment was shown by using the differential thermal analysis (TG-DTA). As shown in FIG. 11, with regard to the PVP used for preparing the thermoelectric layer included in the gas sensor according to the embodiment, it was confirmed that the DTG (mg/s) and the weight rapidly fluctuated at 450° C. Accordingly, as shown FIGS. 10(a) and 10(b), it can be confirmed that the rapid fluctuation in DTA at 456° C. was caused by PVP, based on the differential thermal analysis result of the metal paste.

FIGS. 12 and 13 are graphs showing the thermoelectric properties of the thermoelectric layer included in the gas sensor according to the embodiment of the present invention.

FIG. 12 shows the Seebeck coefficient (μV/K) according to the heat treatment time (min) when the thermoelectric layer included in the gas sensor according to the embodiment is heat-treated at a temperature of 300° C. As shown in FIG. 12, it was confirmed that when the thermoelectric layer included in the gas sensor according to the embodiment is heat-treated at the temperature of 300° C., the Seebeck coefficient value was exhibited as 356 μV/K before the heat treatment, 381 μV/K when heat-treated for 30 minutes, 428 μV/K when heat-treated for 60 minutes, and 391 μV/K when heat-treated for 80 minutes.

FIG. 13 shows the Seebeck coefficient (μV/K) according to the heat treatment temperature (° C.) when the thermoelectric layer included in the gas sensor according to the embodiment is heat-treated for 60 minutes. As shown in FIG. 13, when the thermoelectric layer included in the gas sensor according to the embodiment is heat-treated for 60 minutes, the Seebeck coefficient value was exhibited as 428 μV/K at a temperature of 300° C., but the Seebeck coefficient value gradually decreased as the temperature to be heat-treated later increases, and the Seebeck coefficient value was exhibited as 350 μV/K at a temperature of 350° C.

As shown in FIGS. 12 and 13, it can be seen that the thermoelectric layer included in the gas sensor according to the embodiments of the present invention has the highest thermoelectric properties, when heat-treated at the temperature of 300° C. for more than 50 minutes and less than 70 minutes.

FIGS. 14 and 15 are photographs obtained by photographing the composite structure of the catalyst layer included in the gas sensor according to the embodiment of the present invention.

Referring to FIG. 14(a), the composite structure of the catalyst layer included in the gas sensor according to the embodiment was photographed by using transmission electron microscopy (TEM) at a low magnification of 200 nm. Referring to FIG. 14(b), the composite structure was TEM photographed at a low magnification of 100 nm. As shown in FIGS. 14(a) and 14(b), it was confirmed that, in the composite structure of the catalyst layer included in the gas sensor according to the embodiment, platinum particles were uniformly dispersed and bound onto the surface of graphene.

Referring to FIGS. 15(a) and 15(b), the composite structure of the catalyst layer included in the gas sensor according to the embodiment was TEM photographed at a high magnification of 10 nm. As shown in FIGS. 15(a) and 15(b), it was confirmed that an inter-planar distance corresponding to a plane of platinum cubic structure was 0.22 nm in the composite structure. Accordingly, it can be seen that the platinum particles have a single crystal in the composite structure. In addition, it was confirmed that the selectively grown platinum nanoparticles had a size of 5 nm to 10 nm.

FIG. 16 is a graph showing the properties of the catalyst layer included in the gas sensor according to the embodiment of the present invention.

Referring to FIG. 16, the gas sensor according to the embodiment is prepared in which temperatures (° C.) according to time (min) when reacted with hydrogen having a concentration of 2% and 3%, respectively were exhibited with respect to the case when the catalyst layer contains only platinum, when the catalyst layer contains platinum and graphene at the weight ratio (wt %) of 1:1 (Pt/G 50 wt), and when the catalyst layer contains platinum and graphene at the weight ratio (wt %) of 7:3 (Pt/G 30 wt).

As shown in FIG. 16, it was confirmed that, when the gas sensor according to the embodiment reacts with hydrogen at concentrations of 2% and 3%, the catalyst layer containing platinum and graphene at the weight ratio (wt %) of 1:1 (Pt/G 50 wt) exhibited the highest temperature. In addition, it was confirmed that the catalyst layer containing platinum and graphene together exhibited the higher temperature compared to the temperature of the catalyst layer containing only platinum. Accordingly, it can be seen that the gas sensor according to the embodiment had the improved sensing efficiency when the catalyst layer contains platinum and graphene at the weight ratio (wt %) of 1:1.

FIG. 17 is a graph for comparing changes in the properties upon the heat treatment of the gas sensor according to the embodiment of the present invention.

Referring to FIG. 17(a), hydrogen having a concentration of 50 ppm to 4000 ppm was continuously provided three times (Rep. 1, Rep. 2, and Rep. 3) without heat treating the gas sensor according to the embodiment, and an electromotive force (output voltage) V according to time (min) was measured. As shown in FIG. 17(a), it was confirmed that the electromotive force increased by 32% and 55% when the gas sensor according to the embodiment is not heat-treated.

Referring to FIG. 17(b), the gas sensor according to the embodiment was heat-treated for 1 hour at a temperature of 250° C., hydrogen having a concentration of 50 ppm to 4000 ppm was continuously provided three times (Rep. 1, Rep. 2, and Rep. 3), and the electromotive force (output voltage) V according to time (min) was measured. As shown in FIG. 17(b), it was confirmed that an overall amount of sensitivity change was significantly decreased when the gas sensor according to the embodiment was heat-treated, and the sensitivity change rate exhibited as 2.46% compared to FIG. 17(a) when hydrogen having a concentration of 4000 ppm was provided. In addition, compared to FIG. 17(a), it was confirmed that the overall electromotive force increased 2.37 times from 77.2 μV to 183 μV. In other words, it can be seen that the sensing efficiency may be improved when the gas sensor according to the embodiment is heat-treated for stabilization after preparing the catalyst layer.

FIG. 18 is a graph showing the properties according to the hydrogen concentration provided to the gas sensor according to the embodiment of the present invention.

Referring to FIGS. 18(a) to 18(h), hydrogen having concentrations of 100 ppm, 200 ppm, 400 ppm, 800 ppm, 1000 ppm, 2000 ppm, 3000 ppm, and 4000 ppm was provided to the gas sensor according to the embodiment, and the reaction rate (T90) and the recovery rate (D10) were measured at each hydrogen concentration.

As shown FIGS. 18(a) to 18(h), It was confirmed that the gas sensor according to the embodiment exhibited the reaction rate of 34.6 s and the recovery rate of 5.4 s when hydrogen having a concentration of 100 ppm was provided, the reaction rate of 16.7 s and the recovery rate of 2.5 s when hydrogen having a concentration of 200 ppm was provided, the reaction rate of 9.3 s and the recovery rate of 2.6 s when hydrogen having a concentration of 400 ppm was provided, the reaction rate of 6.1 s and the recovery rate of 2.4 s when hydrogen having a concentration of 800 ppm was provided, the reaction rate of 5.4 s and the recovery rate of 2.4 s when hydrogen having a concentration of 1000 ppm was provided, the reaction rate of 4.2 s and the recovery rate of 2.2 s when hydrogen having a concentration of 2000 ppm was provided, the reaction rate of 3.9 s and the recovery rate of 2.0 s when hydrogen having a concentration of 3000 ppm was provided, and the reaction rate of 4.5 s and the recovery rate of 2.8 s when hydrogen having a concentration of 4000 ppm was provided. In other words, it was confirmed that the hydrogen sensor according to the embodiment exhibited the reaction rate within 30 seconds and the recovery rate within 3 seconds as a whole.

FIG. 19 is a graph showing the reliability of the gas sensor according to the embodiments of the present invention.

Referring to FIG. 19, hydrogen having a concentration of 400 ppm was repeatedly provided to the gas sensor according to the embodiment 10 times, and the electromotive force (output voltage) V according to time (min) was measured. As shown in FIG. 19, as a result of repeatedly providing hydrogen having a concentration of 400 ppm to the gas sensor 10 times, it was confirmed that a reproducibility error was exhibited as 0.45%.

As shown in FIGS. 18 and 19, it can be seen that the gas sensor according to the embodiment of the present invention has excellent sensing efficiency and high reliability.

Although the present invention has been described in detail with reference to the preferred embodiments, the present invention is not limited to the specific embodiments and shall be interpreted by the following claims. Further, it will be apparent that a person having ordinary skill in the art may carry out various deformations and modifications for the embodiments described as above within the scope without departing from the present invention.

The invention claimed is:

1. A gas sensor comprising:
   a substrate;
   a thermoelectric layer disposed on the substrate and including a metal nanowire, wherein the metal nanowire included in the thermoelectric layer has a concentration greater than 60 wt % and less than 85 wt %;
   a first electrode and a second electrode spaced apart from each other on the thermoelectric layer; and
   a catalyst layer disposed on the first electrode and having a composite structure in which a metal particle is bonded to a carbon structure.

2. The gas sensor of claim 1, wherein
   the catalyst layer reacts with a target gas, in which heat is generated in the catalyst layer after the catalyst layer reacts with the target gas;
   the generated heat causes a temperature difference between a first area of the thermoelectric layer in which the first electrode is disposed and a second area of the thermoelectric layer in which the second electrode is disposed; and
   the temperature difference between the first and second areas causes a potential difference between the first area and the second area.

3. The gas sensor of claim 1, wherein the metal nanowire includes at least one of a tellurium nanowire, a $Bi_xTe_y$ nanowire, a $Bi_xSe_y$ nanowire, an $Sb_xTe_y$ nanowire, and a $PbTe_{1-x}Se_x$ nanowire (x>0, y>0).

4. The gas sensor of claim 1, wherein a ratio by weight (wt %) between the carbon structure and the metal particle in the catalyst layer is 1:1.

5. The gas sensor of claim 4, wherein the carbon structure includes graphene and the metal particle includes a platinum particle.

6. The gas sensor of claim 1, wherein the carbon structure and the metal particle form a covalent bond to each other.

7. The gas sensor of claim 1, wherein the first electrode and the second electrode are positioned at a same level based on a top surface of the substrate.

8. A method for manufacturing a gas sensor, the method comprising:
   preparing a substrate;
   forming a thermoelectric layer including metal nanowires on the substrate, wherein forming the thermoelectric layer includes heat-treating the thermoelectric layer at a temperature of 300° C. for more than 50 minutes and less than 70 minutes;
   forming a first electrode and a second electrode spaced apart from each other on the thermoelectric layer; and
   forming a catalyst layer having a composite structure, in which a metal particle is bonded to a carbon structure, on the first electrode.

9. The method of claim 8, wherein the forming of the thermoelectric layer includes:

preparing the metal nanowires;

preparing metal paste by mixing the metal nanowires with a polymer-containing binder and a solvent;

forming the thermoelectric layer by providing the metal paste onto the substrate; and heat-treating the thermoelectric layer.

10. The method of claim 9, wherein at least some of the metal nanowires in the thermoelectric layer are melted or vaporized due to the heat treating, so that the metal nanowires are networked.

11. The method of claim 8, wherein the forming of the catalyst layer includes:

preparing a mixed solution containing the carbon structure;

oxidizing the carbon structure in the mixed solution;

providing a metal precursor to the oxidized carbon structure;

preparing the composite structure in which the metal particle is bonded to the carbon structure, by reducing the carbon structure provided with the metal precursor; and providing the composite structure onto the first electrode.

12. A method for manufacturing a gas sensor, the method comprising:

preparing a substrate;

forming a thermoelectric layer including metal nanowires on the substrate, wherein the thermoelectric layer is formed by providing a metal paste onto the substrate, wherein the metal paste is prepared by mixing the metal nanowires with a polymer-containing binder and a solvent, and wherein the binder includes PVP and the solvent includes at least one of DEG and DEGBE;

forming a first electrode and a second electrode spaced apart from each other on the thermoelectric layer; and forming a catalyst layer having a composite structure, in which a metal particle is bonded to a carbon structure, on the first electrode.

* * * * *